(12) United States Patent
Strölin (10) Patent No.: US 10,473,312 B2
(45) Date of Patent: Nov. 12, 2019

(54) HANDLE DEVICE FOR SURGICAL LIGHT COMPRISING SENSORS AS WELL AS SURGICAL LIGHT

(71) Applicant: KARL LEIBINGER MEDIZENTECHNIK GMBH &CO. KG, Müehlheim (DE)

(72) Inventor: Joachim Strölin, Rietheim (DE)

(73) Assignee: Karl Leibinger Medizintechik GmbH & Co. KG, Muehlheim (DE)

( * ) Notice: Subject to any disclaimer, the term of this patent is extended or adjusted under 35 U.S.C. 154(b) by 0 days.

(21) Appl. No.: 15/745,806

(22) PCT Filed: Jul. 25, 2016

(86) PCT No.: PCT/EP2016/067689
§ 371 (c)(1),
(2) Date: Jan. 18, 2018

(87) PCT Pub. No.: WO2017/025308
PCT Pub. Date: Feb. 16, 2017

(65) Prior Publication Data
US 2018/0209623 A1   Jul. 26, 2018

(30) Foreign Application Priority Data

Aug. 13, 2015 (DE) .......................... 10 2015 113 336

(51) Int. Cl.
*F21V 21/40* (2006.01)
*F21V 23/04* (2006.01)
(Continued)

(52) U.S. Cl.
CPC ............ *F21V 21/403* (2013.01); *A61B 90/30* (2016.02); *A61B 90/35* (2016.02); *A61B 90/361* (2016.02);
(Continued)

(58) Field of Classification Search
CPC . A61B 2090/308; A61B 90/35; A61B 90/361; F21V 21/403; F21V 23/0471; F21V 23/0485
See application file for complete search history.

(56) References Cited

U.S. PATENT DOCUMENTS 6,880,957 B2    4/2005  Walters
7,370,991 B1 *  5/2008  Ellis-Fant .............. A61B 90/35
                                                                 362/105
(Continued)

FOREIGN PATENT DOCUMENTS

CN    1363796 A    8/2002
CN    101233362 A   7/2008
(Continued)

OTHER PUBLICATIONS

Office Action, DE 10 2015 113 336.9 (with attached English Translation), dated May 13, 2016 (pp. 10).
(Continued)

*Primary Examiner* — Sean P Gramling
(74) *Attorney, Agent, or Firm* — Eversheds Sutherland (US) LLP (57) ABSTRACT

The present application relates to a handle device for a surgical light. The handle device may include a grip element which is prepared for being arranged on a lamp holding body of the surgical light and which forms a grip surface at an outer area. A sensor module is detachably connected to the grip element, with the sensor module including at least one distance sensor which is designed for detecting a position of an object. The present application further includes a surgical light including such a handle device.

12 Claims, 7 Drawing Sheets

(51) Int. Cl.
  *A61B 90/30* (2016.01)
  *A61B 90/00* (2016.01)
  *A61B 90/35* (2016.01)
  *F21W 131/205* (2006.01)
  *F21Y 115/10* (2016.01)
  *A61B 17/00* (2006.01)
  *F21W 131/20* (2006.01)

(52) U.S. Cl.
  CPC .............. *F21V 23/0471* (2013.01); *A61B 2017/00203* (2013.01); *A61B 2090/308* (2016.02); *A61B 2090/309* (2016.02); *F21W 2131/20* (2013.01); *F21W 2131/205* (2013.01); *F21Y 2115/10* (2016.08)

(56) References Cited

U.S. PATENT DOCUMENTS

| | | |
|---|---|---|
| 2008/0304281 A1 | 12/2008 | Scholz |
| 2009/0318772 A1 | 12/2009 | Marka et al. |
| 2012/0075832 A1* | 3/2012 | Schmid ................ F21V 21/403 362/33 |
| 2013/0310652 A1 | 11/2013 | Barsoum et al. |
| 2014/0066722 A1 | 3/2014 | Marka et al. |
| 2014/0268751 A1 | 9/2014 | Boccoleri et al. |
| 2015/0003049 A1* | 1/2015 | Chang ................ A61B 1/0692 362/105 |
| 2015/0208478 A1 | 7/2015 | Sattler et al. |
| 2016/0230974 A1* | 8/2016 | Timoszyk .............. A61B 90/30 |

FOREIGN PATENT DOCUMENTS

| | | |
|---|---|---|
| CN | 101608778 A | 12/2009 |
| CN | 102537796 A | 7/2012 |
| CN | 103403442 A | 11/2013 |
| DE | 10 2012 014 716 A1 | 5/2015 |
| EP | 1 728 482 A1 | 12/2006 |
| EP | 2434202 A1 | 3/2012 |

OTHER PUBLICATIONS

Office Action, EP 16 751 515.4-1015 (with attached English Translation), dated Nov. 29, 2018 (pp. 8).
Search Report for CN201680044993.X (in Chinese), dated Jul. 5, 2019 (3 pp.).
Office Action for CN201680044993.X (in Chinese), dated Jul. 15, 2019 (4 pp.).
Office Action for CN201680044993.X (in English), dated Jul. 15, 2019 (6 pp.).

* cited by examiner

HANDLE DEVICE FOR SURGICAL LIGHT COMPRISING SENSORS AS WELL AS SURGICAL LIGHT

TECHNICAL FIELD

The invention relates to a handle device for a surgical light comprising a grip element (also referred to as handle or simply as grip) which is prepared for being arranged on a lamp holding body of the surgical light and which forms a grip surface at an outer area. The invention also relates to a surgical light comprising such handle device.

BACKGROUND OF THE INVENTION

It has been generally known from prior art to provide in surgical lights a certain sensor system which detects an object located between the area to be operated on/the wound area and the lamp holding body of the surgical light. In this context, it is also known that, when the object, for example a body part (e.g. head) of a person partly covers the bundles of light beams generated by individual lights/single lamps of the surgical light, the covered single lamps are weakened as to their brightness/illuminance or are even switched off. The residual single lamps of the surgical light that are not covered by the object may at the same time be lighted up so as to still enable intense illumination uniformity of the wound area. In the case of said surgical lights the sensors are usually incorporated directly inside the lamp holding body of the surgical light.

In this way, it is already possible to reduce or even avoid the intensity of the light radiation of the surgical light and the related heat development on the object, for example an operating surgeon's head. It has turned out to be a drawback in said known systems, however, that the surgical lights equipped with the sensor system usually are relatively complicated and thus also cost-intensive to manufacture due to the increased manufacturing expenditure. Also, due to the still relatively small number of clients desiring such sensor system at all, it has been relatively inefficient so far to mass-produce said surgical lights tightly connected to the sensor system. Especially for those end consumers who are not primarily interested in said sensor system frequently such surgical light is too expensive.

SUMMARY OF THE INVENTION

It is thus the object of the present invention to eliminate said drawbacks known from prior art and to offer a surgical light which is especially profitable when it is mass-produced, but which is intended to be individually retrofittable with a sensor system.

According to the invention, this object is achieved by the fact that a handle device is provided, wherein a sensor module is detachably connected to the grip element thereof and the sensor module includes at least one distance sensor which is designed for detecting a position of an object (i.e. for measuring a distance between the object and the handle device/sensor module).

Said modular design enables, if the end consumer of a surgical light additionally desires a sensor system, the existing handle device to be easily replaced with a handle device of the type according to the invention. The known handle devices anyway are usually connected to the lamp holding body in a replaceable manner anyway in order to remove them for the purpose of sterilization. In this way, the surgical light may be individually retrofitted especially easily with the sensor module including a distance sensor.

Further advantageous embodiments are claimed in the subclaims and will be explained in detail in the following.

It is moreover of advantage when the sensor module includes a housing in which the at least one distance sensor is received/arranged/attached. In this way, a most robust design of the sensor module is configured and the distance sensor is protected from the environment.

Furthermore, it is also advantageous when in the sensor module plural distance sensors are present the measuring fields/effective areas of which are directed away from each other (starting from the housing) with their respective central axis/directional axis. Hence an as comprehensive detection as possible of the area below the lamp holding body is realized in the operating condition.

In this context, it is further advantageous when the housing includes/forms a disk-shaped cavity portion inside of which the at least one distance sensor is arranged/attached. In this way, the sensor module has an especially compact design and occupies as little space as possible.

When in the area of the at least one distance sensor the housing is designed to be permeable to a measuring signal to be detected by the at least one distance sensor (preferably infrared-transparent), the at least one distance sensor is accommodated in the housing in an especially advantageous manner protected from the environment.

When the at least one distance sensor moreover is designed as an infrared sensor, the sensor module is equipped with proven measuring sensors which permit even lower-cost manufacture of the sensor module/handle device.

It is also useful when the sensor module includes a handle receiving portion which is detachably connected to the grip element. This allows to replace a handle element rendered non-sterile with a new/sterile grip element in an especially simple manner without having to remove the sensor module as well. In addition, this enables different grip elements to be connected to the sensor module.

In this context, it is also advantageous when the handle receiving portion forms a receiving journal onto which in at least one operating condition of the handle device a sleeve portion of the grip element including the grip surface is attached/slipped, i.e. is positively arranged. In this way, an especially stable support of the grip element relative to the sensor module is materialized.

It is also advantageous in this context when the grip element is connected to the sensor module via a form fitting and/or a load-carrying connection in at least one operating condition, as in this way the grip element can be replaced especially quickly.

It is further advantageous when the sensor module includes a computer unit (also referred to as computing unit) which is electrically connected to the at least one distance sensor and generates control signals for controlling the surgical light in response to the measuring data established by means of the at least one distance sensor. This helps to materialize an especially direct electric connection/supply of the at least one distance sensor. During operation, the surgical light is directly controlled in response to said control signals such that the respective luminous elements/single lamps irradiating the object/the operating surgeon can be dimmed or even switched off.

Moreover, it is of advantage when a voice control unit for actuating the at least one distance sensor and/or for controlling the surgical light in at least one operating condition is integrated in the sensor module. The voice control unit which, further preferred, includes at least one microphone, i.e. a sound sensor, permits to individually control the individual lights of the surgical light. Also, numerous further functions may be realized by means of said voice control unit and, for example, control signals may be generated for varying the height adjustment or the inclination of the surgical light. In this way, direct contact of the operating surgeon with the surgical light can be avoided in service.

In this context, it is furthermore also useful when the voice control unit is electronically connected to the computing unit/computer unit. Hence the voice control unit is used directly with already present the computer unit for evaluating the measuring data of the distance sensors. The structure of the sensor module is kept relatively simple with an even more cost-effective manufacture being materialized.

Moreover, the invention also comprises a surgical light including a handle device according to at least one of the afore-mentioned embodiments, wherein the handle device is connected to a lamp holding body of the surgical light in an at least partly detachable manner, thus allowing the sterilizability of the handle device to be materialized in an especially simple manner.

In this context, it is also advantageous when the sensor module is detachably arranged on the lamp holding body, as then the sensor module can be quickly removed from the surgical light, if required, after having been fastened before. Thus, the surgical light especially can be individually equipped.

When a computing unit of the sensor module is electrically connected to a central control unit of the surgical light, control signals can be directly transmitted from the sensor module to the surgical light, thus allowing the surgical light to individually and directly adjust its individual lights (especially as regards its illumination intensity/brightness). The control of the surgical light thus is realized as directly as possible.

In accordance with the invention, a sensor system is thus equipped with distance sensors which are accommodated in the central handle unit/handle device of the surgical light. Said central handle unit is easily replaceable per se, thus allowing a surgical light to be retrofitted very easily and quickly with the sensors, even in the case of replacement purchase. There are different variants of handle groups/handle devices, wherein there is provided one without sensors and one with sensors (according to the invention) which then may be easily exchanged. In a further variant, the sensor module is interposed as an intermediate ring between the handle group and the lamp holding body. The central arrangement of the sensors and of the central handle unit within the surgical light thus enables optimum "view" of the sensors to the heads of the operating surgeons/users. The sensors detect the head as an obstacle and then fade out the portions located there behind. The sensors are equipped on a ring-shaped printed board. The round/conical component (side wall of the housing/of the cavity portion) is designed to be transparent, i.e. IR transparent.

BRIEF DESCRIPTION OF THE DRAWINGS

Hereinafter the invention will be illustrated in detail by way of Figures; in this context, also different embodiments will be described; wherein.

DETAILED DESCRIPTION

The Figures are merely schematic and exclusively serve for the comprehension of the invention. Like elements are provided with like reference numerals. The features of the different embodiments may also be freely combined with each other.

Figure 1:
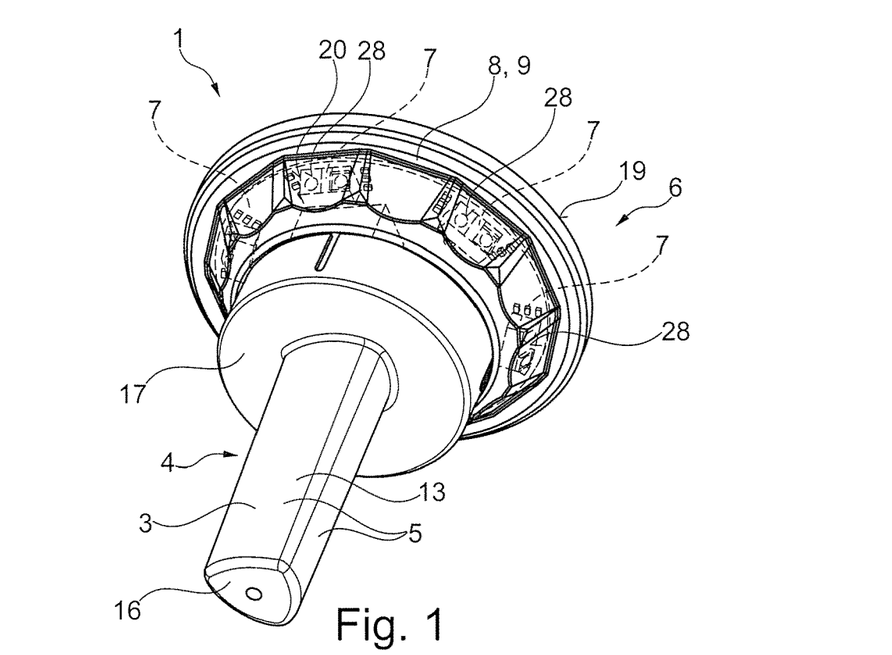
FIG. 1 shows an isometric representation of a handle device according to the invention in accordance with a first embodiment in which a grip element is tightly connected to a sensor module, FIG. 2 hows an isometric representation of the handle device of FIG. 1, wherein now merely the sensor module is shown and the grip element is removed from a receiving journal of the sensor module, and wherein the voice control unit is evident behind the outer wall of the housing shown to be slightly transparent.

First of all, in FIG. 1 a handle device 1 according to the invention in accordance with an advantageous first embodiment is clearly visible. The handle device 1 is prepared for assembly/for temporary mounting to a surgical light 10 described in detail hereinafter in FIGS. 5 to 9 and 11 to 13. Thus, the invention does not only relate to the handle device 1 itself but also to a surgical light 10 comprising such handle device 1.

The handle device 1 includes a grip element 3 prepared for being arranged on a lamp holding body 2 of the surgical light 10, the grip element 3 also being simply referred to as handle. The grip element 3 consequently is dimensioned so that it may be seized by a hand of a person such as an operating surgeon, so as to move the surgical light 10 in an operating condition of the handle device 1 in which it is tightly connected to the lamp holding body 2 of the surgical light 10 into the desired position. The surgical light 10 hereinafter described in detail (e.g. in connection with FIGS. 5 and 6) further includes a supporting structure not shown here for the sake of clarity which is connected to the lamp holding body 2 and by which the lamp holding body 2 can be positioned at will.

On an outer area 4 of the grip element 3 a grip surface 5 is formed which the operating surgeon in service contacts for varying the position of the surgical light 10. The grip element 3 per se has a rod-like hollow sleeve portion 13 which extends lengthwise. Said grip surface 5 is formed directly on the outer peripheral side/outer shell side thereof The grip element 3 is configured at the outer area 4 thereof such that it has as smooth a surface/grip surface 5 as possible which can be easily sterilized. This is to say that the roughness of the grip surface 5 is chosen so that cleaning with subsequent sterilization can be easily carried out and dirt particles are prevented from being caught.

The sleeve portion 13 includes a cover 16 protecting/closing off the interior of the sleeve portion 13 toward the environment at a front end which in service faces away from the lamp holding body 2. Therefore, the cover 16 forms a first axial end area of the sleeve portion 13 of the grip element 3. By a second end area opposed to the first end area the sleeve portion 13 merges into a disk-shaped enlarged portion 17. The enlarged portion 17 and the sleeve portion 13 are made from one material piece, i.e. are integrally connected to each other.

A sensor module 6 according to the invention is in turn connected to the grip element 3. The sensor module 6 is detachably connected to the grip element 3. The sensor module 6 is positively and frictionally connected to the grip element 3. The sensor module 6 which is visible in its entirety in FIG. 2 in a state dismounted from the grip element 3 in turn includes a housing 8. The housing 8 in turn includes a disk-shaped cavity portion 9 or, resp., is formed by said disk-shaped cavity portion 9. The disk-shaped cavity portion 9 is sealed toward the environment. The cavity portion 9, on the one hand, is formed by two walls spaced apart from each other—a front wall 18 and a rear wall 19—. On the other hand, the cavity portion 9 has an annularly extending side wall 20 which connects the front wall 18 to the rear wall 19. The front wall 18 is the flatly extending wall of the cavity portion 9 which in service faces the grip element 3, whereas the rear wall 19 of the housing is the flatly extending wall of the cavity portion 9 which in service faces away from the grip element 3.

Furthermore, the sensor module 6 includes, apart from the housing 8, a handle receiving portion 11 which is tightly connected to the housing 8/cavity portion 9. Said handle receiving portion 11 is tightly connected to the front wall 18 of the cavity portion 9. The handle receiving portion 11 constitutes a receiving journal 12 which perpendicularly extends away from the front wall 18 of the cavity portion 9 extending in an imaginary plane of extension. Consequently, a longitudinal axis 32 of the receiving journal 12 extends perpendicularly to the front wall 18 and, resp., to the plane of extension thereof.

Figure 4:
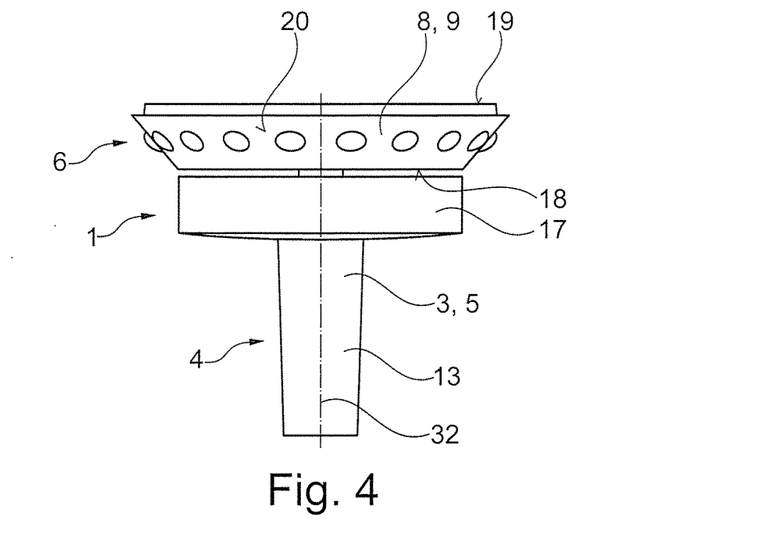
FIG. 4 is a schematic side view of the handle device according to FIG. 1, wherein the arrangement between the housing/sensor module and the grip element is evident.

The receiving journal 12 is dimensioned and adapted to the sleeve portion 13 of the grip element 3 such that it can be inserted into the sleeve portion 13. In the assembled state of the handle device 1 as shown in FIG. 1 said receiving journal 12 is positively and frictionally inserted into the sleeve portion 13. The grip element 3 therefore is positively and frictionally connected to the sensor module 6. As is also evident from the schematic representation according to FIG. 4, the enlarged portion 17 in this assembled state is kept at a distance from the front wall 18 in the axial direction of the receiving journal 12 (corresponding to the axial direction of the longitudinal axis 32 and, resp., of the sleeve portion 13).

Figure 2:
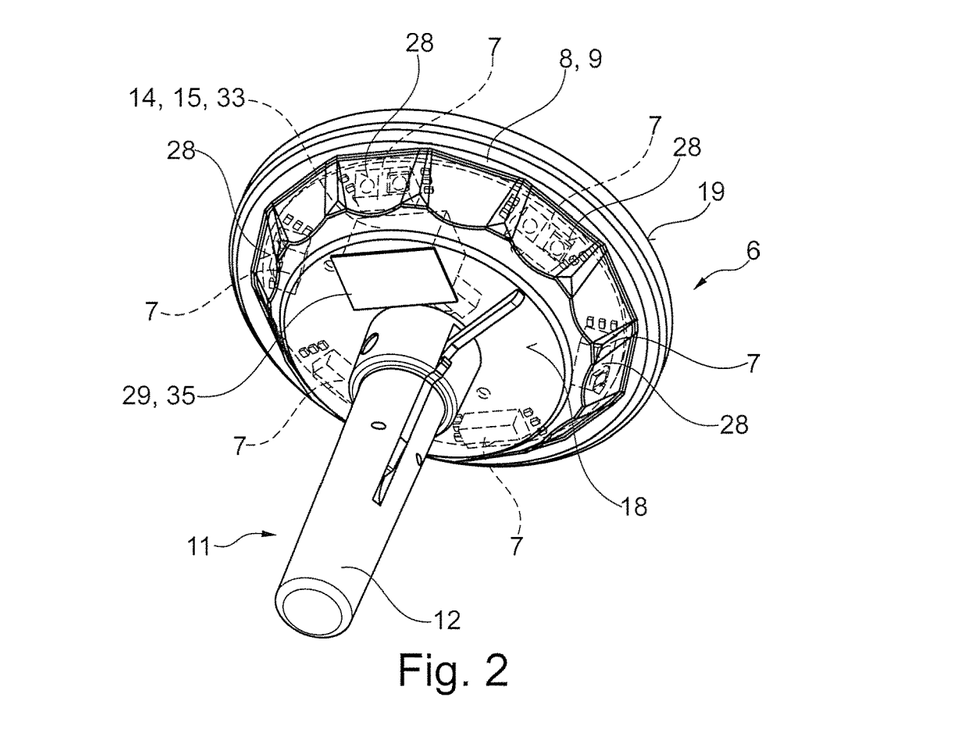
Figure 3:
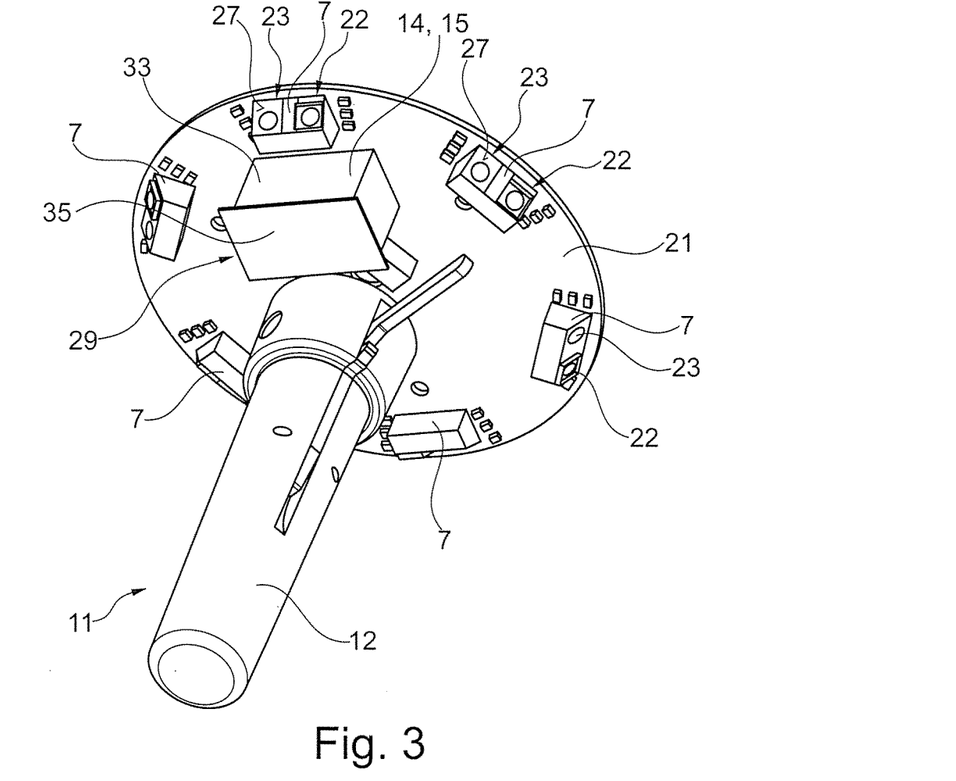
FIG. 3 is an isometric representation of part of the sensor module according to FIG. 2, wherein the interior of the housing in which the printed board receiving the receiving sensors is arranged is evident.

Finally, in FIG. 3 the inner structure of the sensor module 6 is illustrated. For the sake of clarity, as compared to FIG. 2 the housing 8/the cavity portion 9 is omitted in FIG. 3 so that the electronic unit of the sensor module 6 can especially clearly identified. According to the invention, plural distance sensors 7 are positioned on a disk-shaped printed board 21 of said electronic unit. All of said distance sensors 7 are equally designed and working.

The distance sensors 7 are in the form of infrared sensors (also referred to as infrared distance sensors). Each distance sensor 7 has a substantially drop-shaped/balloon-shaped effective area 24 within which an object 25 such as the head of an operating surgeon can be detected. For this purpose, infrared light is emitted by an infrared transmitter 22 of the distance sensor 7, which infrared light spatially spreads substantially in funnel/cone shape along an imaginary directional axis 26. Apart from the infrared transmitter 22, the distance sensor 7 also includes an infrared receiver 23. The infrared receiver 23 is designed and configured so that, when an object 25 is present inside the effective area 24, it detects, by measurement, part of the infrared light emitted by the infrared transmitter 22 before which is reflected by the object 25. The effective area 24 can be identified especially clearly from FIG. 9, wherein in this Figure the handle device 1 is mounted already on the surgical light 10. The part of infrared light reflected by the object 25 is therefore supplied to the infrared receiver 23 which converts the reflected infrared light to a control signal. In response to the distance of the object 25 from the distance sensor 7/from the infrared receiver 23 the infrared receiver 23 detects the signal at an earlier or later point in time relative to the time of transmission of the infrared light by the infrared transmitter 22. In this way, the distance between the object 25 and the handle device 1 is easily detectable. The effective area 24 is thus restricted by the shape of the emitted infrared light as well as the reach of the infrared receiver 23. Each distance sensor 7 therefore is designed to detect/establish a position of the object 25 in an area between the lamp receiving housing 2 and a wound area via the distance of the object 25 relative to the distance sensor 7 and, resp., to the sensor module 6.

The distance sensors 7 are arranged on the printed board 21 such that the effective area 24 thereof is aligned with its directional axis 26 extending transversely/obliquely to the longitudinal axis 32 of the receiving journal 12, especially preferably offset from said longitudinal axis 32 by approx. 45°. The infrared transmitter 22 and the infrared receiver 23 are arranged/orientated in a receiving plane 27 which is orientated perpendicularly to the directional axis 26.

Figure 14:
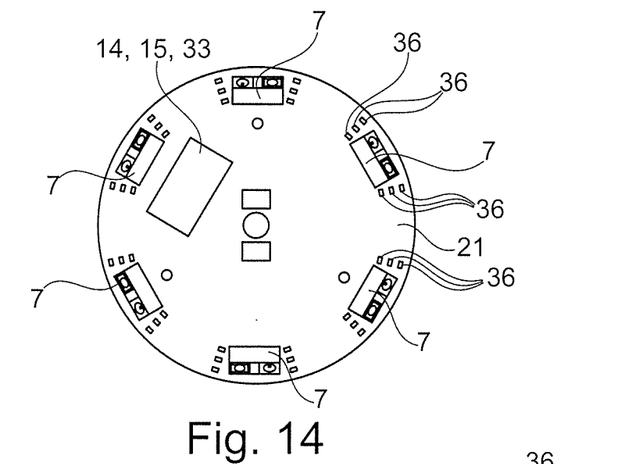
FIG. 14 shows an inner side, i.e. a side facing the interior of the cavity portion of the printed board of the sensor module already shown in FIG. 3.

In this embodiment, six distance sensors 7 are spread substantially along a circular imaginary peripheral line around the longitudinal axis of the receiving journal 12, wherein in further embodiments also different numbers of distance sensors 7 are selected, however, for example fewer or more than six, preferably seven, eight, nine or at least ten distance sensors 7. In FIG. 14 the distribution of the distance sensors 7 is once again schematically illustrated, with the computer unit 14 having no microphone 29 in this view for the sake of clarity. The distance sensors 7 are arranged at equal distances along the imaginary peripheral line and have a substantially equal distance from the longitudinal axis 32 of the receiving journal 12. The distance sensors 7 are arranged and orientated so that they are adapted to detect, by their effective areas 24, the position of an object 25 inside the entire periphery, i.e. within an angular area of 360° around the longitudinal axis 32.

As is especially clearly evident also from FIGS. 1 and 2, the side wall 20 of the housing 8 is configured to have plural cover areas 28. Each cover area 28 extends in parallel to the receiving plane 27 and therefore conically between the front wall 18 and the rear wall 19. The circular front wall 18 has a smaller diameter than the equally circular rear wall 19. The side wall 10 in this configuration is made from a material which is permeable to the measuring signals of the distance sensors 7. Consequently, this side wall 20 is transparent to infrared light. Since the conically shaped housing 8/the conically shaped cavity portion 9 in its entirety consists of the same material, it is made, in its entirety, from an infrared-transparent material. Apart from the infrared-transparent side wall 20, thus also the front wall 18 is infrared-transparent. Consequently, a cover area 28 extending in parallel to the receiving plane 27 of the distance sensor 7 is associated with each of the latter, the cover area extending substantially over the same width as the respective distance sensor 7. Each of the distance sensors 7 is further electronically connected to a computer unit 14 arranged on the printed board 21. Said computer unit 14 is configured especially for transmitting, in a condition in service connected to the surgical light 10, control signals to the surgical light 10 and, resp., to the (central) control unit thereof, which is not shown in detail here for the sake of clarity, so that, according to the established position of the object 25, the individual lights/single lamps 30 of the lamp fields 31 of the surgical light 10 illuminating the object 25 can be dimmed or appropriately switched off.

Moreover, in this computer unit 14, i.e. in an electronics housing 33 accommodating the computer unit 14 a voice control unit 15 is integrated. The voice control unit 15 in turn is electrically connected to the computer unit 14. As a consequence, acoustic signals recorded by a microphone 29 of the voice control unit 15 can be converted to an appropriate control signal by means of the computer unit 14 and in turn can be transmitted, in a condition arranged on the surgical light 10, to the central control unit of the latter. In FIG. 3 a sound-permeable external covering of the microphone 29 projects from the electronics housing 33 to all sides. In this way, the surgical light 10 can be operated also individually by individual voice instructions. Apart from operating the brightness/illumination intensity of the respective single lamps 30 of the surgical light 10, it is also possible to vary, for example, a position of the surgical light 10 by means of said voice instructions. The voice control unit 15 also includes a loudspeaker.

As is clearly evident from FIG. 2, the front wall 18 of the cavity portion 9 includes an appropriate recess into which the membrane/external covering 35 of the microphone 29 designed to be sound-transmitting is inserted. Consequently, sound transmission is facilitated through the housing 8 into the interior.

In another embodiment, the computing unit 14 is not connected wire-bound to the central control unit of the surgical light 10, as in the present case, but is connected wirelessly, preferably via Bluetooth.

Figure 5:
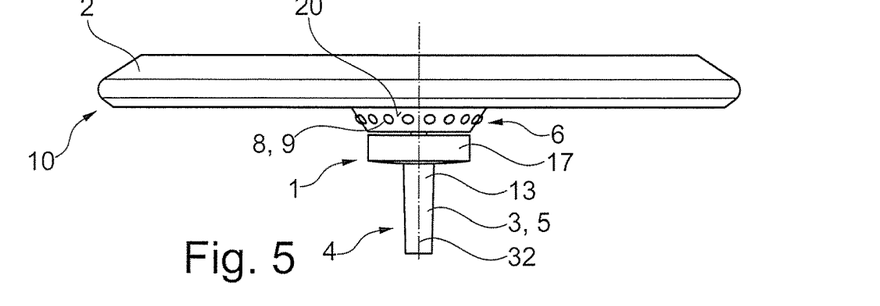
FIG. 5 is a side view of a surgical light according to the invention in accordance with a first advantageous embodiment, wherein the handle device is schematically represented as already in FIG. 4 and is mounted on a lamp holding body of the surgical light.
Figure 6:
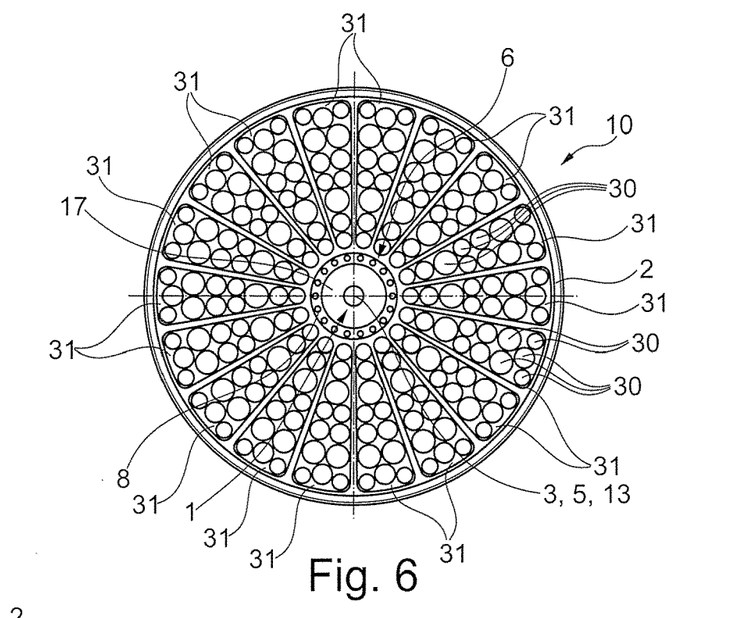
FIG. 6 is a bottom view of the surgical light shown in FIG. 5, wherein the different lamp fields of the surgical light each of which includes a plurality of single lamps and which in service illuminate the wound area can be especially clearly identified.

In FIGS. 5 and 6 also a surgical light 10 according to the invention including a mounted handle device 1 according to FIGS. 1 to 4 is especially clearly visible. The surgical light 10 includes the lamp holding body 2, also referred to as base body, into which plural single lamps 30 are inserted. The individual single lamps 30 in this embodiment are combined/grouped with further single lamps 30 to form different lamp fields 31. In this configuration, the surgical light 10 has a substantially disk-shaped and housing-type lamp holding body 2 which in further configurations also has different designs and may be formed in several parts, i.e. from several lamp holder segments, for example. Each of the lamp fields 31 (also referred to as luminous fields) is driven and structured in a substantially equally working manner.

Each lamp field 31 has the same number of single lamps 30. The single lamps 30 of a lamp field 31 vary as to size and/or brightness/light intensity/illumination intensity. The light color of the various single lamps 30 is also varying. Each lamp field 31 is in the form of a cake-shaped piece of the total number of single lamps 30 extending disk-shaped around the central handle device 1. Each of the single lamps 30 comprises exclusively one LED, in further configurations also plural LEDs, however. Each single lamp 30 includes a lens/lens optics associated with the LED. Accordingly, each of the single lamps 30 is electrically connected to the central control unit of the surgical light 10 and is controllable in response to the control signals on the side of the central control unit independently of each other, and especially controllable as to its light intensity/light color.

As is evident in connection with FIGS. 9 and 11 to 13, in service of the surgical light 10 monitoring of an area which is illuminated by the single lamps 30 is materialized by means of the distance sensors 7. The individual distance sensors preferably act within a reach of more than one, preferably more than two meters in the direction of the directional axis 26. In this way, due to an object 25 moving into the light beam/into the bundle of light beams of a single lamp 30 according to FIGS. 11 to 13, the distance between the object 25 and the sensor module 6 is detected by the distance sensors 7 and then a control signal is generated by the computer unit 14, thus causing, by means of the central control unit, the single lamps 30 of the respective lamp fields 31 (i.e. the single lamps 30 which directly illuminate the object by their bundles of light beams) to be dimmed and switched off, respectively. Dimming is effectuated in this case depending on the height distance between the surgical light 10 and the object 25. As is clearly visible from FIGS. 11 to 13, the lamp fields 31 according to FIG. 13 may be switched off/dimmed in total or the single lamps 30 of the lamp fields 31 may be switched off/dimmed individually depending on the position of the object 25 relative to the handle device 1/distance sensor 7.

Figure 15:
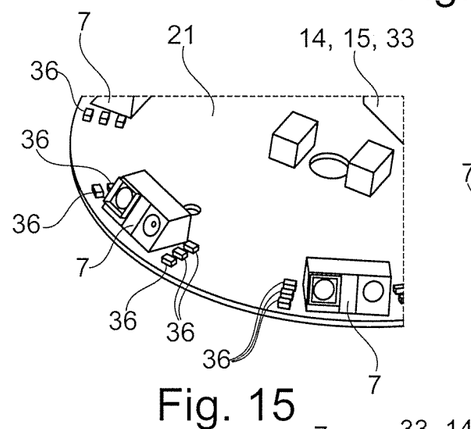
FIG. 15 shows an isometric detailed view of the printed board of FIG. 14 in the area of two adjacent distance sensors, with the indicator lamps thereof being clearly visible.

For indicating whether an object 25 is present in the effective area 24 of the respective distance sensor 7, for each distance sensor 7 moreover plural indicator lights 36 are arranged on the printed board 21, which are especially clearly evident from FIG. 15. If an object 25 is present in the effective area 24 of the respective distance sensor 7, the number of luminous/switched-on indicator lights 36 increases with a decreasing distance between the distance sensor 7 and the object 25. In this configuration, six indicator lights 36 are provided for each distance sensor 7. Each indicator light 36 is in the form of an LED. It is also possible to switch between different indicator lights 36 which differ by their light color depending on the distance between the distance sensor 7 and the object 25.

The handle device 1 in its mounted state is fastened centrally on the lamp holding body 2 and thus with the longitudinal axis 32 is arranged coaxially to an imaginary central axis of the lamp holding body 2.

Furthermore, also the microphone 29 has a reach of at least one, especially preferred of at least two meters, thus allowing acoustic sources generating a corresponding acoustic control signal, for example the object 25 itself, to be detected so as to appropriately control the surgical light 10.

Figure 7:
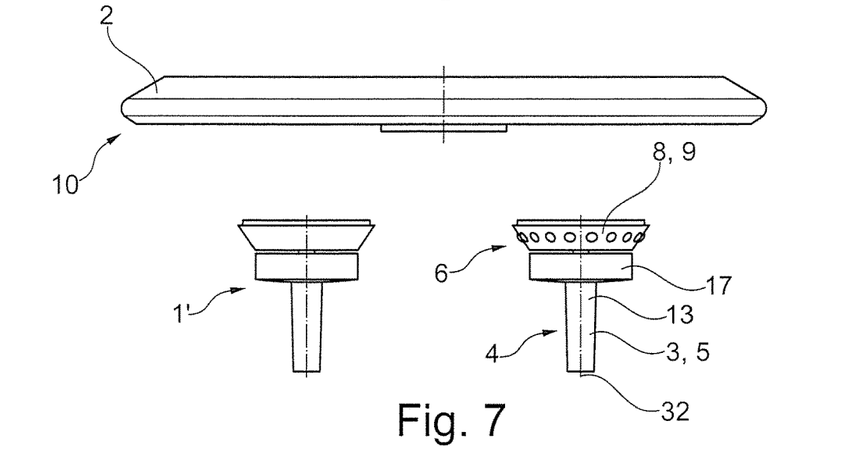
FIG. 7 is a schematic lateral representation of a surgical light comprising two different handle devices provided in a dismounted state, wherein the right one of the two shown handle devices is the handle device of the type of the invention according to FIGS. 1 and 4, respectively, and the left one of the two handle devices is a handle device known from prior art, with both of the handle devices being adapted to be attached to the shown lamp holding bodies of the surgical light.
Figure 8:
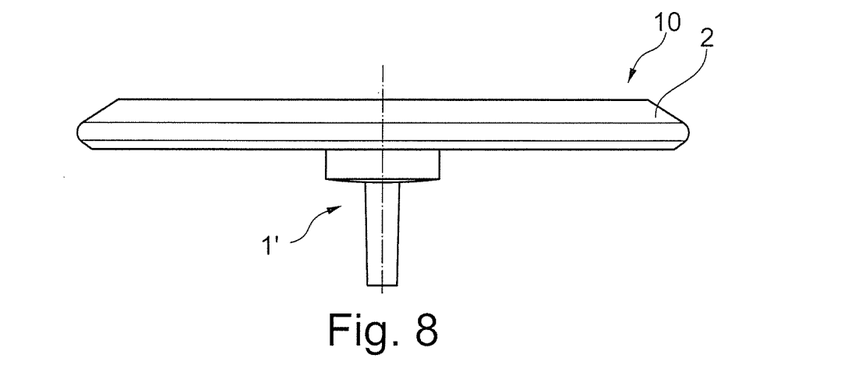
FIG. 8 shows a prior art surgical light, i.e. comprising a handle device without the sensor module according to the invention.
Figure 9:
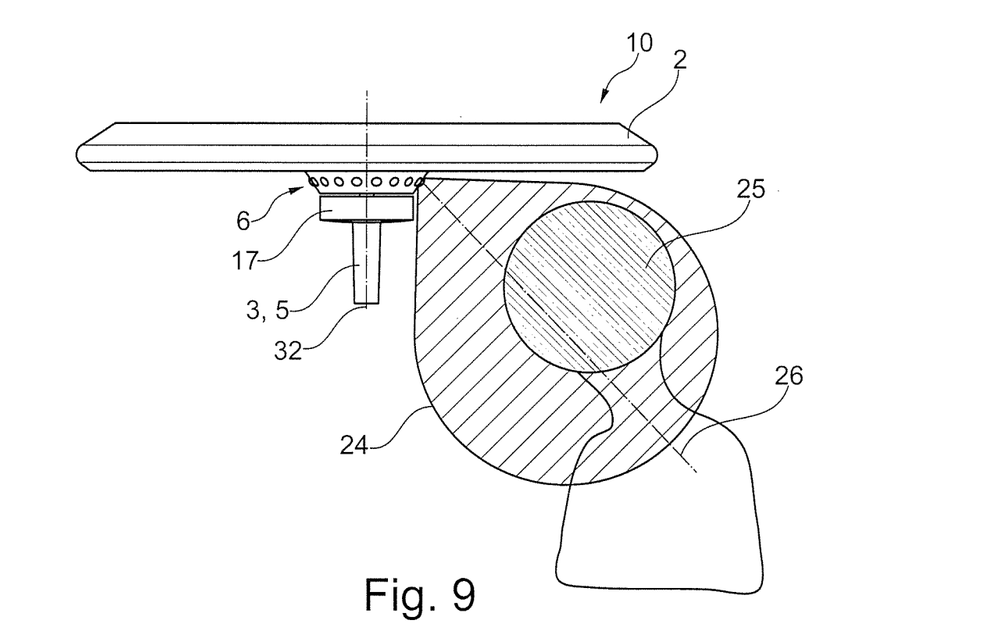
FIG. 9 is a schematic side view of a surgical light according to the invention in accordance with FIGS. 5 and 6, wherein an effective area of a distance sensor of the sensor module generated in service can be especially clearly identified and wherein in the effective area of the distance sensor an object, viz. a person's head, is located.

In FIGS. 7 and 8, the advantageous configuration of the handle device 1 as well as the interaction with the surgical light 10 can once again be identified especially clearly. In this way, it is easy to replace a conventional prior art handle device 1', as illustrated in FIG. 8 and on the left side in FIG. 7, with a handle device 1 according to the invention, as illustrated on the right side in FIG. 7, by removing the detachable part of the former handle device 1' from the surgical light 10 and fastening the handle device 1 according to the invention to the lamp holding body 2. For this purpose, on the rear wall 19 of the cavity portion 9 the sensor module 6 forms a detachable portion which is detachably connected to the lamp holding body 2. For this purpose, the cavity portion 9 is connected positively and frictionally, preferably detachably/releasably via sort of a bayonet fitting to the lamp holding body 2. In this way, the completely mounted position of the surgical light 10 and, resp., of the handle device 1 is realized, as it is shown in FIG. 9, for example. Also, an image recording means not shown in detail here for the sake of clarity which includes at least one video camera for recording the wound area and is controllable by the voice control unit 15 is integrated in the sensor module 6.

Figure 16:
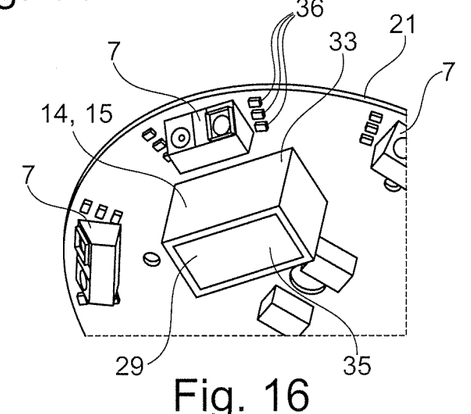
FIG. 16 is an isometric detailed view of a printed board of a handle device in accordance with another advantageous embodiment, with the computer unit thereof being clearly visible.
Figure 17:
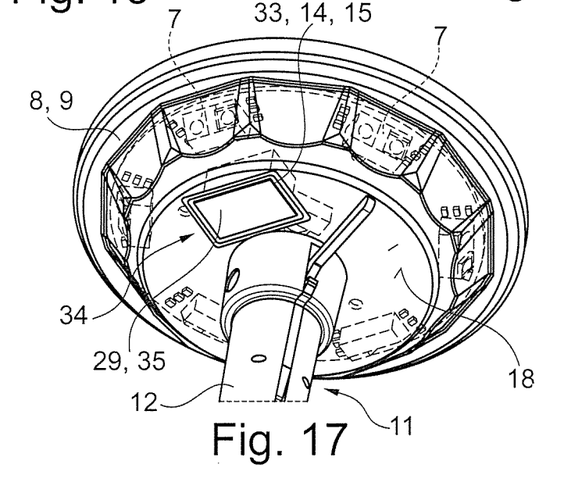
FIG. 17 is an isometric representation of a handle device according to another advantageous embodiment into which the printed board according to FIG. 16 is inserted.

In connection with FIGS. 16 and 17, another embodiment of the handle device 1 according to the invention is schematically represented, said handle device 1 working and being configured in accordance with the first embodiment. As a difference in this case, the external cover 35 of the microphone 29 is inserted in a frame formed by the electronics housing 33 and thus is positively retained in the electronics housing 33 in an especially clever way. From FIG. 17 it is evident that in the housing 8 of the sensor module 6, viz. in the front wall 18 thereof, a recess 34 corresponding to the electronics housing 33 is formed into which recess the electronics housing 33 projects from the side of the outer cover 35.

Figure 18:
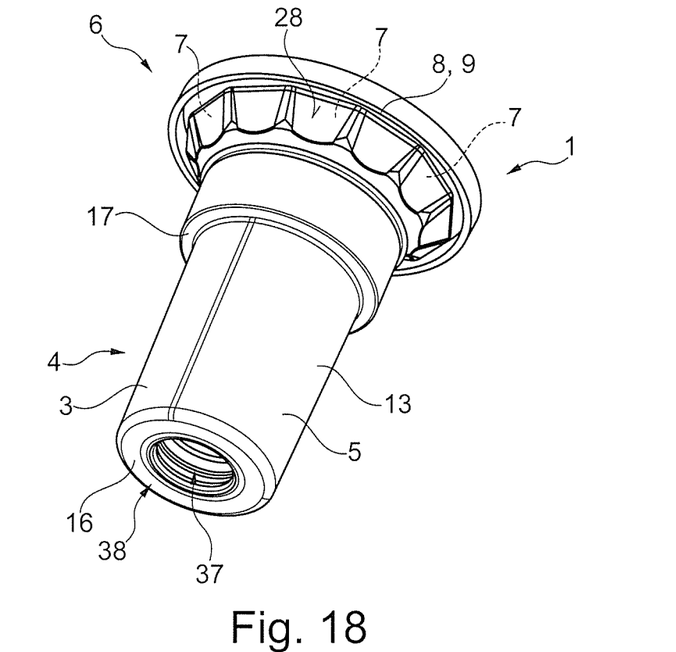
FIG. 18 is an isometric representation of a handle device according to another advantageous embodiment into which a video camera is integrated.
Figure 19:
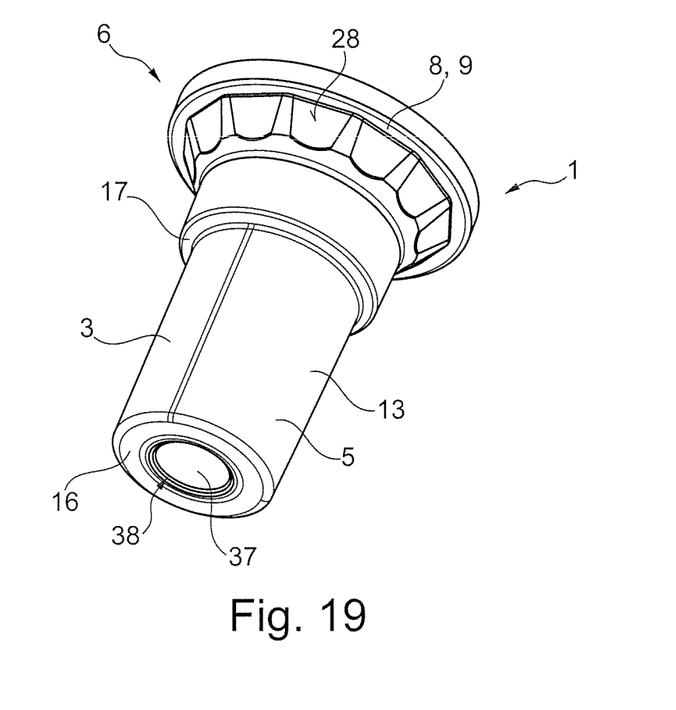
FIG. 19 is an isometric representation of the handle device according to FIG. 18, wherein the housing of the sensor module now is no longer shown to be transparent.

FIGS. 18 and 19 equally illustrate another embodiment of the handle device 1 according to the invention, wherein said handle device 1 works and is configured according to the first embodiment. In this case, in particular the grip element 3 is designed to be thicker, however. This is due to the fact that a video camera 37 for recording the wound area is arranged within the grip element 3. The outermost glass of the lens of the video camera 37 is visible, with the light admission axis of the video camera 37 being concentric with respect to a through hole 38. The video camera 37 is surrounded by the grip surface 5, but in the area of the cover 16 it is provided with the through hole 38 through which the video camera 37 detects the exterior of the handle device 1.

Figure 10:
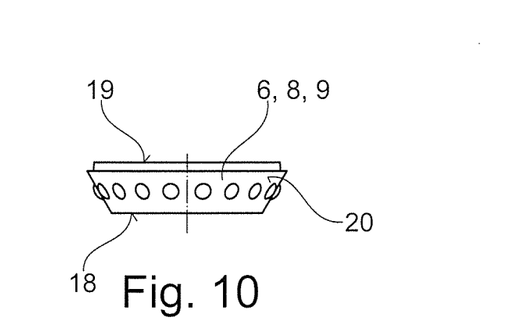
FIG. 10 is a schematic side view of a sensor module for a handle device according to an advantageous further embodiment, wherein the sensor module in this case is ring-shaped and has no receiving journal.
Figure 11:
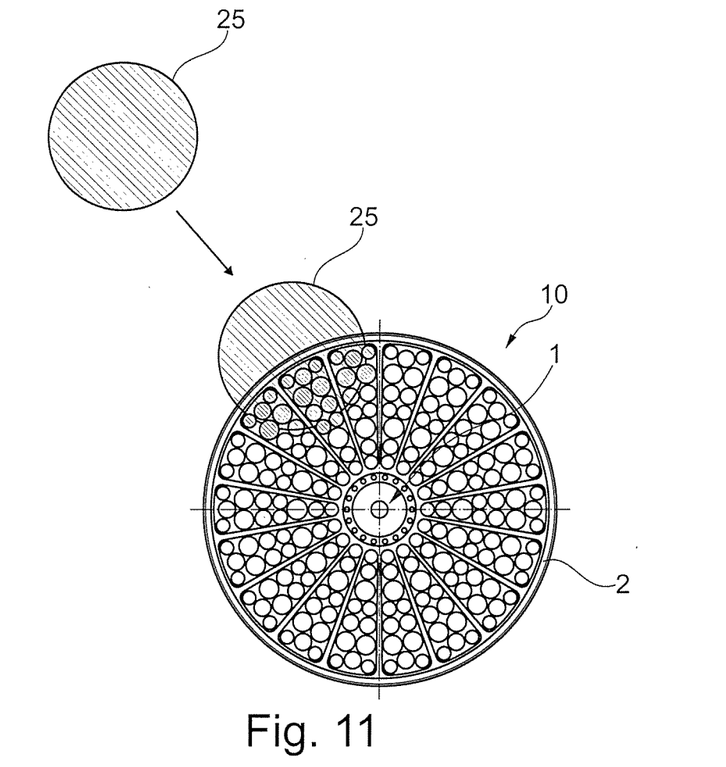
FIG. 11 is a schematic bottom view of the surgical light according to the invention, wherein, just as in FIG. 9, within reach of the sensor module and the distance sensors thereof, resp., a round object as marked by the arrow is moved into the bundles of light beams of individual lamp fields, whereupon the dark single lamps of the lamp fields are automatically dimmed with the aid of a computer unit due to the detected position by means of at least one distance sensor.
Figure 12:
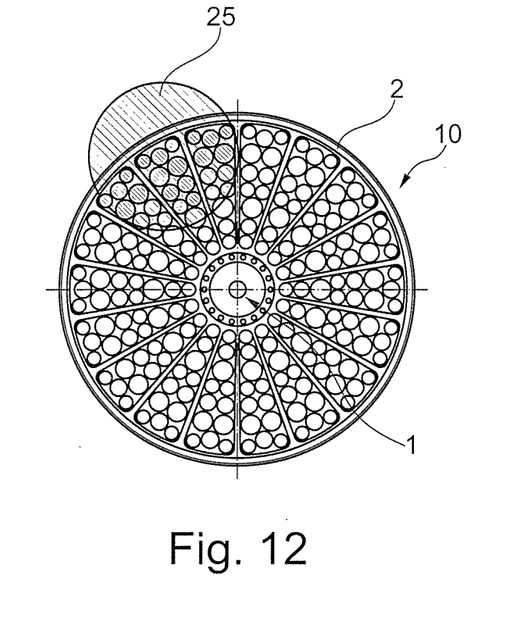
FIG. 12 is a bottom view of the surgical light according to FIG. 11, wherein the object now is moved further into the direction of the central handle/central handle device and, as compared to FIG. 11, further single lamps of the lamp fields are switched off, FIG. 13 again is a bottom view of the surgical light according to FIGS. 11 and 12, wherein the object, as compared to FIG. 12, is moved further in the direction of the center, i.e. in the direction of the handle device and after that even further single lamps of the surgical light are dimmed/switched off.
Figure 13:
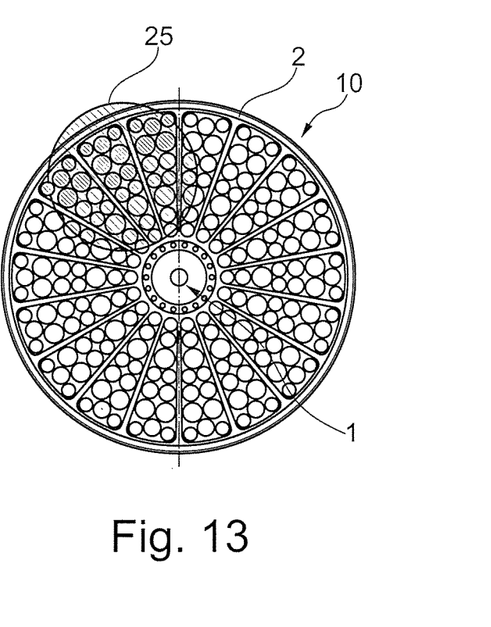

In connection with FIG. 10, another embodiment of the handle device according to the invention is disclosed, wherein primarily a further sensor module 6 having an alternative design is evident. The sensor module 6 only consists of the afore-described disk-shaped cavity portion 9 in the form of an intermediate ring forming the housing 8. A handle receiving portion 11 in the form of a receiving journal 12 is omitted in this case. This embodiment materializes the fact that an existing handle device 1 is detachably connected directly to the housing 8. Therefore, it is also possible in this way to provide a detachable sensor module 6. The structure and the functioning of the latter correspond to the sensor module 6 of the first embodiment.

In other words, a handle device 1 in the form of a central handle unit is materialized. The sensors in the form of the distance sensors 7 are arranged within said central handle unit 1 in the surgical light 10. From here the sensors 7 are provided with optimum "view" (range of view corresponds to effective range 24) to the heads 25 of the users. The sensors 7 detect the head 25 as an obstacle and fade out the portions of the lamp fields 31 located there behind/the corresponding single lamps 30. The sensors 7 are mounted on a ring-shaped printed board 21. The round/conical component, viz. the side wall 20, is transparent (IR transparent).

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

REFERENCE NUMERALS

1 handle device
1' prior art handle device
2 lamp holding body
3 grip element
4 outer area
5 grip surface
6 sensor module
7 distance sensor
8 housing 9 cavity portion
10 surgical light
11 handle receiving portion
12 receiving journal
13 sleeve portion
14 computing unit
15 voice control unit
16 cover
17 enlarged portion
18 front wall
19 rear wall
20 side wall
21 printed board
22 infrared transmitter
23 infrared receiver
24 effective area
25 object
26 directional axis
27 receiving plane
28 cover area
29 microphone
30 single lamp
31 lamp field
32 longitudinal axis
33 electronics housing
34 recess
35 external cover
36 indicator light

I claim:

1. A handle device for being detachably arranged on a surgical light, comprising: a sensor module, a grip element which forms a grip surface at an outer area, wherein the sensor module is detachably connected to the grip element, wherein the sensor module includes a housing accommodating a plurality of distance sensors each of which distance sensors is designed for detecting a position of an object beyond the housing, and wherein the distance sensors are arranged inside a disk-shaped cavity portion of the housing and central axes of measuring fields of the distance sensors are directed away from each other.

2. The handle device according to claim 1, wherein in the area of each of the distance sensors the housing is configured to be permeable to a measuring signal that is to be detected by each of the distance sensors.

3. The handle device according to claim 1, wherein at least one distance sensor is an infrared sensor.

4. The handle device according to claim 1, wherein the sensor module includes a handle receiving portion which is detachably connected to the grip element.

5. The handle device according to claim 2, wherein a handle receiving portion forms a receiving journal onto which a sleeve portion of the grip element including the grip surface is attached in at least one operating condition of the handle device.

6. The handle device according to claim 1, wherein the grip element is connected to the sensor module via a form fitting and/or a load-carrying connection in at least one operating condition.

7. The handle device according to claim 1, wherein the sensor module includes a computer unit which is electrically connected to each of the distance sensors and generates control signals for controlling the surgical light in response to the measuring data established by means of each of the distance sensors.

8. The handle device according to claim 1, wherein a voice control unit for operating each of the distance sensors and/or for controlling the surgical light in an operating condition is integrated in the sensor module.

9. The handle device according to claim 6 wherein a voice control unit is electronically connected to a computer unit.

10. A surgical light comprising a handle device according to claim 1, wherein the handle device is at least partially detachably connected to a lamp holding body of the surgical light.

11. The surgical light according to claim 8, wherein the sensor module is detachably arranged on a lamp holding body.

12. The surgical light according to claim 8, wherein a computer unit of the sensor module is electrically connected to a central control unit of the surgical light.

* * * * *